United States Patent [19]

Lefrancier et al.

[11] 4,335,111
[45] Jun. 15, 1982

[54] COMPOUNDS ASSOCIATING PEPTIDYL OF AMINOACYL RESIDUES TO LIPOPHILIC GROUPS AND PHARMACEUTICAL COMPOSITIONS CONTAINING SAID NEW COMPOUNDS

[75] Inventors: Pierre Lefrancier, Bures sur Yvette; Edgar Lederer, Sceaux; Jean Choay; Louis Chedid, both of Paris, all of France

[73] Assignee: Agence National de Valorisation de la Recherche (ANVAR), Neuilly Sur Seine, France

[21] Appl. No.: 106,022

[22] Filed: Dec. 21, 1979

[30] Foreign Application Priority Data

Dec. 22, 1978 [GB] United Kingdom ............... 49887/78

[51] Int. Cl.$^3$ ..................... A61K 37/00; A61K 37/02; C07C 103/52
[52] U.S. Cl. ............................ 424/177; 260/112.5 R; 260/404; 260/404.5; 260/413; 424/312
[58] Field of Search ..................... 260/112.5 R, 413 S, 260/413 R, 404, 404.5 A, 404.5 R; 424/177, 312

[56] References Cited

U.S. PATENT DOCUMENTS 4,101,536 7/1978 Yamamura et al. ......... 260/112.5 R

FOREIGN PATENT DOCUMENTS 2015534 12/1979 United Kingdom .

*Primary Examiner*—Blondel Hazel
*Attorney, Agent, or Firm*—Weiser, Stapler & Spivak

[57] ABSTRACT

The invention relates to new compounds associating peptidyl or aminoacyl residues to lipophilic groups and pharmaceutical compositions containing said new compounds.

The compounds according to the invention have the general formula:

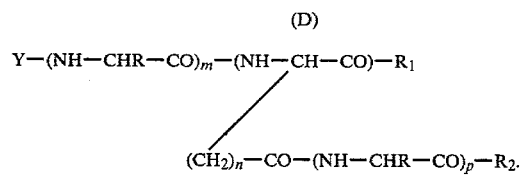

A preferred compound is:

1-O
 (L-alanyl-D-isoglutaminyl-L-alanyl)-glycerol-3-mycolate.

These compounds are useful as anti-infectious agents.

36 Claims, No Drawings

COMPOUNDS ASSOCIATING PEPTIDYL OF AMINOACYL RESIDUES TO LIPOPHILIC GROUPS AND PHARMACEUTICAL COMPOSITIONS CONTAINING SAID NEW COMPOUNDS

The invention relates to new compounds having useful biological and pharmacological properties, particularly immuno-stimulant, anti-infectious properties and more particularly antibacterial properties.

The invention also relates to the pharmaceutical compositions as well as to standard biological reagents which contain these compounds.

The compounds according to the invention correspond to the general formula $$\begin{array}{c} \text{(D)} \\ Y-(NH-CHR-CO)_m-(NH-CH-CO)-R_1 \\ \diagdown \\ (CH_2)_n-CO-(NH-CHR'-CO)_p-R_2 \end{array} \quad \text{(I)}$$

in which:
—(NH—CHR—CO) and (NH—CHR'—CO) independently from each other are residues of aminoacids of the group containing glycine, alanine, β-alanine, arginine, asparagine, cysteine, glutamine, histidine, hydroxyproline, isoleucine, leucine, methionine, phenylalanine, proline, serine, threonine, tryptophane and valine;
m is zero or 1,
n is 1 or 2,
p is 0, 1, 2 or 3,
Y is either H or an acyl group with up to 4 carbon atoms
$R_1$ and $R_2$ are the same or different, at least one of them being a lipophilic group comprising a hydrocarbon chain containing at least 10 carbon atoms.

One of the $R_1$ and $R_2$ groups may advantageously be selected from —OH, OCH$_3$, OC$_2$H$_5$, OC$_3$H$_7$, alcoxy groups up to to —OC$_9$H$_{19}$, —NH$_2$, an amino group mono or disubstituted by lower alkyl group up to 9 carbon atoms. Preferably, it is $R_2$ which forms the lipophilic group.

In a preferred class of compounds according to the invention, the abovesaid lipophilic group is an —OX, or —OCH$_2$—CH$_2$O—COX or —OCH$_2$—CHOH—CH$_2$O—COX, or NHX group wherein: X is an alkyl linear or branched saturated or unsaturated group optionally containing hydroxyl, carbonyl, carboxyl, or aryl groups the latter being possibly substituted, or a cyclopropane ring, whereby X comprises at least 10 carbon atoms.

Particularly, preferred classes of compounds according to the invention are those in which X comprises more than 30 carbon atoms, such as from 80 to 90 carbon atoms.

Particularly the invention concerns the mycolic ester derivatives, thus those in which X comprises a number of carbon atoms ranging from 80 to 90 (for instance average number of 86 in the mycolates referred to hereafter).

In a preferred group of compounds according to the invention n is 2. In a preferred sub-group within that group m is 1 and the aminoacyl residue NH—CHR—CO is a L-alanyl residue.

Thus preferred compounds of the invention are those which can be represented as:

L-ala-D-isoGln-(NH—CHR'—CO)p-R$_2$, wherein "isoGln" stands for "isoglutaminyl".

In a further preferred group of compounds the NH—CHR'—CO aminoacyl residue(s) is (or are) L-aminoacyl residue(s).

Another group of preferred compounds according to the invention comprises the compounds of formula 1 in which R$_2$ is formed of said above defined lipophilic group, for instance —OX, OCH$_2$—CH$_2$O—COX or —OCH$_2$—CHOH—CH$_2$O—COX, or —NHX.

Among the various possible R$_2$ the following groups are preferred: glycerol-mycolate, glycerol-corynomycolate.

In particular, the coryno-mycolic acid is the synthetic α-tetradecyl-β-hydroxy octodecanoic acid.

Particularly preferred compounds according to the invention are:

1-O(L-alanyl-D-isoglutaminyl-L-alanyl)glycerol-3-mycolate which can be represented by the formula:

$$\begin{array}{ccc} \text{(L)} & \text{(D)} \\ H_2N-CH-CO-NH-CH-CONH_2 \\ | & | \\ CH_3 & (CH_2)_2 \\ & | \\ & CO-NH-CH-CO-OCH_2CH(OH) \\ & | & | \\ & CH_3 & CH_2OOC-C_{86}H_{172}O \\ & \text{(L)} \end{array}$$

(or L-Ala-D-isoGln-L-Ala-OCH$_2$CH(OH)-CH$_2$OOC-C$_{86}$H$_{172}$O)

1-O-(L-alanyl-D-isoglutaminyl)-glycerol-3-mycolate
1-O-(L-alanyl-D-isoglutaminyl-L-alanyl)-glycerol-3-coryno-mycolate
1-O-(L-alanyl-D-isoglutaminyl)-glycerol-3-corynomycolate, of formula:

L—Ala—D—isoGln—L—Ala—O—CH$_2$—CHOH—CH$_2$OOC—CH—CH(OH)(CH$_2$)$_{14}$CH$_3$
|
C$_{14}$H$_{29}$ 1-O-(D-isoGln-Ala)-glycerol-3-mycolate
1-O-(β-Ala-D-isoGln-L-Ala)-glycerol-3-mycolate
1-O-(L-Ala-D-isoAsn-L-Ala)-glycerol-3-mycolate
wherein "isoAsn" is "isoasparaginyl")
1-O-(L-Ala-D-Gln-L-Ala)-glycerol-3-mycolate
(wherein "Gln" is "glutaminyl")
1-O-(L-Ala-D-isoGln-L-Ala)-0-n-C$_{10}$H$_{21}$=DP-L-Ala-decylester.

1-O-(L-Ala-D-isoGln-L-Ala)-0-n-C$_{15}$H$_{31}$=DP-L-Ala-pentadecylester

1-O-(L-Ala-D-isoGln-L-Ala)-OCH$_2$—CHOH—CH$_2$OOC—C$_{17}$H$_{25}$, designated as: (DP-L-Ala)-glycerol-3-stearate

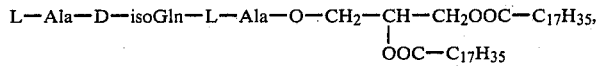

designated as: (DP-L-Ala)-glycerol-2,3-di-stearate.

In the preceding compounds another aminoacyl residue may be substituted for the first L-alanyl residue, such as glycyl, L-seryl, L-valyl, L-prolyl. In the same manner another aminoacyl residue such as arginine, asparagine, cysteine, glutamine, histidine, hydroxyproline, isoleucine, leucine, methionine, phenylalanine, threonine, tryptophane, may be substituted for the second L-alanyl residue, particularly in the preceding first and third compounds.

A most preferred compound is:

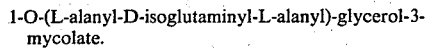

The invention also relates to salts, particularly pharmaceutically acceptable salts of the above defined compound, particularly the salts which the free amine groups of the compounds according to the invention may form with pharmaceutically acceptable acids.

For preparing the compounds according to the invention, the known methods of peptide synthesis may be resorted to. During the various operations the functional groups which should not react are protected by usual blocking groups, these being ultimately removed at the end of the preparation.

The invention also relates to the pharmaceutical compositions containing the compounds according to the invention and particularly to these compositions intended to be used for the treatment of infectious diseases. More particularly the invention concerns compositions containing the said compounds to prevent or cure bacterial infections, particularly those involving bacteria which develop in the blood circulatory system. They are useful against pathogenic germs which are resistant to antibiotics.

These compositions are all the more interesting as they are well tolerated and particularly they are not antigenic and have no pyrogenic effect. Furthermore, their therapeutic index is very satisfactory.

These compositions contain in addition to the said compounds of formula(I) a pharmaceutically acceptable vehicle suitable for the route of administration (oral, parenteral, etc).

Preferred pharmaceutical compositions are formed of sterile injectable solutions or suspensions or liposomes containing an effective dose of a product according to the invention and free of pyrogenicity. Compositions of this kind are preferably solutions or dispersions in an aqueous medium such as saline solutions.

Other preferred compositions are those which contain a liquid or solid vehicle suitable for oral administration. For example, they may be prepared as tablets, pills, syrups for oral administration. Other preferred compositions are prepared in the form of aerosols, gels, lotions, ointments for the application on mucous membranes.

Pharmaceutical compositions according to the invention are preferably formed in unit doses containing from 10 to 10,000 μg of a compound I.

Other features of the invention will be given below with more details, in examples of preparation and pharmacological testing of products according to the invention.

(A) Synthesis of peptide-glycerol-3-mycolate derivatives (1) Preparation of 1-O(L-alanyl-D-isoglutaminyl-L-alanyl)-glycerol-3-mycolate Tosyl-glycerol-3-mycolate (A)

816 mg tosylchloride were added, in portions of 136 mg, to a solution of 3.78 g (2.96 mmol) of glycerol-3 mycolate, as extracted from mycobacterium bovis, in 70 ml of anhydrous pyridine at −10° C. The reaction was maintained during 72 hours; the pyridine hydrochloride formed was then precipitated with toluene and filtered.

The product was obtained after chromatography on silicagel (type C column, Merck) with a chloroform-ether (95-5) mixture as eluant. 2.708 g of product were recovered.

t-butyloxycarbonyl-L-alanyl-glycerol-3-mycolate (B)

A solution of 3 g (2.09 mmol) of (A) in anhydrous benzene was added to a 40 ml benzene solution of 680 mg (2.98 mmol) of the potassium salt of BOC-L-alanine and of 400 mg of 18-crown-6 ether. The reaction mixture was refluxed for 6 hours, filtered and washed with benzene.

The resulting syrup was passed twice on a column of silicagel 60) and the product eluted with benzene-ether (65 v/35 v). 1.957 g. of product were recovered (yield 64%).

1-O-(L-alanyl)-glycerol-3-mycolate hydrochloride (C)

400 mg (0.273 mmol) of (B) were dissolved in 3 ml glacial acetic acid. 5 ml of a N hydrochloric acid solution in acetic acid were added 45 min. later; the mixture was concentrated and dried under vacuum. 347.5 mg of product (C) were obtained (yield 91%).

BOC-1-O-(L-alanyl-D-isoglutaminyl-L-alanyl)-glycerol-3-mycolate (D)

105.5 mg (0.275 mmol) of BOC-L-alanyl-D-isoglutamine (LEFRANCIER and BRICAS, 1967.Bull.Soc.Chim. Biol., 49, 1757–1271) were dissolved in 5 ml of a tetrahydrofuran-dimethyl-formamid (4-1) mixture. The mixture was cooled at −15° C., and 0.03 ml N-methylmorpholine and 0.036 ml of isobutyl-chloroformiate were then added thereto. Five minutes later a previously cooled (−15° C.) solution of 347 mg (0.27 mmol) of product (C) and 0.03 ml of N-methylmorpholine in 2 ml tetrahydrofuran was added. The mixture was maintained at −15° C. during 4 hours then brought to room temperature. It was washed successively with a solution of K HCO$_3$ (M), with a 10% citric acid solution and with water till the pH remained constant. The organic phase was dried with Na$_2$SO$_4$ and yielded after concentration a syrup which appeared non homogenous on thin layer chromatography (silicagel) with chloroform-methanol (5 v/1 v) as eluant. 377 mg of product were recovered.

Finally, the product was passed on a column of silica gel (Merck-60) with a methanol-chloroform gradient (from 99 v/1 v to 9 v/1 v, 500 ml). 252 mg of product were obtained (yield 60.5%). This product was totally hydrolyzed (HCl 6 N), 110° C. for 20 hours under vacuum and analyzed for the aminoacids to give a molar ratio of alanine to glutamic acid of 2.02 (theory 2.00).

1-O-(L-alanyl-D-isoglutaminyl-L-alanyl)-glycerol-3-mycolate-trifluoroacetate (E)

252 mg (0.151 mmol) of product (D) were dissolved in 3 ml of chloroform; 0.6 ml trifluoro-acetic acid were added. Removal of the t-butyloxycarbonyl was achieved within 1 hour. The mixture was concentrated and dried under vacuum. The product was dissolved in acetic acid at 60° C. then lyophilized. 250 mg (98%) were recovered $[\alpha]_D^{20} = +5.8$ in chloroform (C=0.5).

The formula of the compound obtained as a result of analysis was $C_{100}H_{189}O_{11}N_4F_3 \cdot 4CH_3COOH$.

| Analysis | C | H | N |
|---|---|---|---|
| Calculated | 67.53 | 10.75 | 2.91 |
| Found | 67.59 | 10.24 | 2.96 |

Other Preparations

The passage from the above trifluoroacetate salt to any other salt of the L-alanyl-D-isoglutaminyl-L-alanyl-glycerol-3-mycolate, preferably a pharmaceutically acceptable salt (ascorbate, paratoluol-sulfonate, etc) can be achieved by any method conventional in protein synthesis, for instance by means of the ion exchange procedure. Thus from the preceding trifluoroacetate salt was obtained the hydrochloride acid corresponding to the other desired salt, for instance the: 1-O-(L-alanyl-L-isoglutaminyl-L-alanyl)-glycerol-3-mycolate hydrochloride. $[\alpha]_D^{20} = 3,22$ (chloroform).

| Analysis | C | H | N |
|---|---|---|---|
| Calculated | 71.1 | 11.5 | 3.25 |
| Found | 71.79 | 11.4 | 3.33 |

Analogous compounds in which the peptide chain is modified may be obtained in the same way. Each time the corresponding peptide is coupled with L-alanyl-glycerol-3-mycolate.

The abovesaid glycerol-3-mycolate derivatives can also be prepared by direct binding of the adequate glyceryl-mycolate derivative to the corresponding aminoacyl or peptide moiety, e.g. according to WANG (J. Org. Chem. 42 (1977) 1286).

The following compounds were prepared according to the same scheme as that used for making the abovementioned L-Ala-D-isoGln-L-Ala-glycerol-3-mycolate-trifluoracetate, starting from the L-Ala-glycerol-3-mycolate and the corresponding aminoacyl or peptide moieties.

a. 1-O-(D-isoGln-L-Ala)-glycerol-3-mycolate hydrochloride, $[\alpha]_D^{20} = -4°$ (0.5 CHCl$_3$)
b. 1-O-(β-Ala-D-isoGln-L-Ala)-glycerol-3-mycolate hydrochloride, $[\alpha]_D^{20} = +3°,2 (0.4$ CHCl$_3$)
c. 1-O(L-Ala-D-isoAsn-L-Ala)-glycerol-3-mycolate, $[\alpha]_D^{20} = +3°,5$ (0.4 CHCl$_3$)
d. 1-O-(L-Ala-D-Gln-L-Ala)-glycerol-3-mycolate, $[\alpha]_D^{20} = 2°,95$ (0.45 CHCl$_3$)

Similarly other examples of compounds according to the invention were prepared from either the L-Ala-n-decylester or the L-Ala-n-pentadecylester.

L-Ala-D-isoGln-L-Ala-n-decylester hydrochloride, $[\alpha]_D^{20} = 19°6$ (0.6 CH$_3$OH)

L-Ala-D-isoGln-L-Alan-n-pentadecylester hydrochloride, $[\alpha]_D^{20} = 1,9°$ (0.5 CH$_3$COOH)

(B) Synthesis of peptide-glyceryl-corynomycolates (1) Synthesis of 1-O-(L-Ala-D-isoGln-L-Ala-) glycerol-3-corynomycolate α-corynomicolic acid (I) synthetized according to POLONSKY and LEDERER.Bull.Soc. Chim. France (1954) 504 was purified from its β isomer and of the side products of the reaction (particularly palmitic acid) by chromatography under pressure (on a CHROMATOSPAC 10 chromatographer manufactured by JOBIN and YVON on a column of silica gel H manufactured by MERCK (10×40 cm) and by elution with a chloroform-hexane-acetic acid mixture (50-50-1) (volumic proportions), at a rate of 20 ml/mn). The detection was performed at 254 mμ. Fractions of 15 ml were collected and assayed by thin layer chromatography on silica gel using a mixture of chloroform-benzene-methanol-acetic acid (volumic proportions of 55-50-5-0,1). A pure 40% α-corynomycolic acid solution was obtained (MP 60°-62° C.).

Glycerol-1-α-corynomycolate (II)

396.5 mg of tosyl-glycerol (1.6 mmole) dissolved in 5 ml of a chloroform-benzene mixture (1/1) were dissolved in a solution of 861.5 mg of potassium-α-corynomycolate (1.6 mmole) and of 225 mg of 18-Crown-6, which had been previously solubilized under heat within 10 ml of anhydrous benzene, according to the method of De HAAS and Van DEENEN Recueil. Trav. Chim. Pays-Bas 80 (1961) 951-970. The reaction mixture was refluxed under anhydrous conditions. 28 hours later the suspension was diluted with one volume of benzene and filtered. The filtrate was concentrated to dryness whereby a semi-crystalline syrup was obtained which was then purified on a column of silica gel G (Merck) by eluting it with a chloroform-hexane-methanol mixture (5-5-1), then further by elution under pressure on a column of silica H (Merck) with a chloroform-hexane-methanol mixture (5-5-0.5) whereby a syrup containing the desired compound was obtained: 430 mg (47%).

1-O Tosyl-glycerol-α-3-corynomycolate (III)

215.5 mg of tosyl chloride (1.13 mmole) were added portionwise to 430 mg (750 mμ) of the compound (II) dissolved in 10 ml of anhydrous pyridin maintained at 0° C. 18 hours later the reaction mixture was concentrated to dryness at room temperature and then triturated in toluene. The organic phase was then concentrated to dryness and the product obtained purified on a column of silica gel by elution in the chloroform-ether mixture (95/5):292 mg (53%) of purified product were finally obtained.

Starting from product (III), the synthesis then went on as disclosed in connection with the preceding example, whereby the following products were successively obtained:

1-O(BOC-L-Ala)-glycerol-3-corynomycolate (IV)
1-O-(L-Ala)-glycerol-3-corynomycolate hydrochloryde (V)
1-O-(BOC-L-Ala-D-isoGln-L-Ala)-glycerol-3-corynomycolate (VI).

The final compound obtained:
1-O-(L-Ala-D-isoGln-L-Ala)-glycerol-3-corynomycolate $[\alpha]_D^{20} = 1°,7$ (c=0.45 CHCL$_3$) was obtained.

(C) Synthesis of:

1-O-(L-Ala-D-isoGln-L-Ala)-glycerol-3-stearate

1-O-(L-Ala-D-isoGln-L-Ala)-glycerol-2,3-distearate

Preparation of 1-Tosyl-glycerol-3-stearate (I) and -2,3 distearate (II)

15.7 ml of stearoyl chloride dissolved in 50 ml of anhydrous stearoyl chloride were added dropwise within 1 hour to 46 mmoles of 1-O-tosyl-glycerol dissolved in 100 ml of anhydrous chloroform containing 4.25 ml of anhydrous pyridin at 0° C., according to the method of De HAAS and Van DEENEN Recueil. Trav. Chim. Pays-Bas 80 (1961)(951–970). After 24 hours at room temperature the reaction mixture was diluted by 150 ml of ether and poured in 150 ml of ice-cold 0.5 NH$_2$SO$_4$. The organic phase obtained was washed with ice-cold solutions of HN$_2$SO$_4$ and of half-saturated aqueous solutions of NaCl, then dried on Na$_2$SO$_4$ and concentrated. Ether was added to the syrup obtained and left overnight at $-10°$ C. After filtration there were obtained 3.2 g of 1-tosyl-glycerol-2,3-distearate (III): MP=55°–57° C.

Upon adding methanol to the filtrate and incubating at $-15°$ C., there was obtained a precipitate of 1-tosyl-glycerol-3-stearate (I) which was crystallized in petroleum ether: 4.8 g MP: 58° C.

Starting then from compounds (I) and (II) the syntheses were then carried out according to the methods of preparation referred to in example (A) for the corresponding steps, whereby the following intermediate compounds were first obtained:

1-O-(L-Ala)-glycerol-3-stearate
1-O-(L-Ala)-glycerol-2,3-distearate
1-O-(BOC-L-Ala-D-isoGln-L-Ala)-glycerol-3-stearate
1-O-(BOC-L-Ala-D-isoGln-L-Ala-glycerol-2,3-distearate Finally the following compounds were obtained:

1-O-(L-Ala-D-isoGln-L-Ala)-glycerol-3-stearate hydrochloride, $[\alpha]_D^{20} = -5°,56$ (Benzene)
1-O-(L-Ala-D-isoGln-L-Ala)-glycerol-2,3-distearate hydrochloride, $[\alpha]_D^{20} = -3°,4$ (Benzene).

Compounds in which R$_2$ is —OCH$_2$—CH$_2$—O—COX can be prepared according to the method described by ZAORAL et al for the preparation of similar compounds (Collect. Tchecoslov.Czev. Chem. Commun. 32,1967,843).

Biological Properties

I-Anti-infectious activity (1) Comparative activity of N-acetyl-muramyl-L-alanyl-D-isoglutamine (MDP) and L-alanyl-D-isoglutaminyl-L-alanyl-glyceryl-mycolate Groups of mice were inoculated intramuscularly or intravenously with a dose of Klebsiella pneumoniae (intramuscular challenge with $1.5 \times 10^4$ organisms) which causes death of most of them in the control groups within the week following inoculation. For comparative purposes some of the groups were also treated with N-acetyl-muramyl-L-alanyl-D-glutamine (MDP) and glycerol-3-mycolate.

The products to be tested were injected intravenously 24 hours before the inoculation. Survival was determined 3,5 and 10 days after inoculation. The percentage of protection indicated in table I hereafter denotes the difference of the percentages of survivors in the treated group and in the corresponding control group respectively.

TABLE I

| Treatment i.v. - 24 H | Infection | day 0 | day 3 | day 5 | day 10 | % protection |
|---|---|---|---|---|---|---|
| Controls | 3.10$^4$K.p. i.m. | 24 | 13 | 9 | 8 | |
| MDP 100 μg | | 24 | 20 | 12 | 12 | 17 |
| "compound" 100 μg | | 24 | 23 | 20 | 17 | 37 |
| Controls | 4.10$^3$K.p. i.v. | 24 | 4 | 2 | 2 | |
| MDP 100 μg | | 24 | 21 | 16 | 16 | 58 |
| "Compound" 100 μg | | 24 | 21 | 21 | 21 | 79 |
| Glyceryl-mycolate 100 μg | | 8 | 1 | 1 | 1 | |

"Compound" is the 1-O—(L—Ala—D—isoGln—L—Ala)—glycerol-3-mycolate.

The results of table I show that the products according to the invention exhibit a good anti-infectious activity, as evidenced by the comparative data obtained with N-acetyl-muramyl-L-alanyl-D-isoglutamine (MDP). Glyceryl-mycolate was devoid of significant activity.

(2) Anti-infectious activity of doses of 100 μg of other compounds according to the invention The results obtained in assays ran with 1-O-(L-Ala-D-isoGln-L-Ala)-glycerol-3-mycolate and other compounds are indicated in table II hereafter.

It is observed that at the dose of 100 μg, best results were obtained when the compounds of the invention included a lipophilic group comprising more than 30 C-atoms, particularly and advantageously at least 31 C-atoms (1-O-(-L-Ala-D-Gln-L-Ala)-glycerol-3-corynomycolate) and any of the following peptide sequences:

1-O-(L-Ala-D-isoGln)-;
1-O-(-L-Ala-D-isoAsn)-;
1-O-(-D-isoGln-L-Ala)-;
1-O-(-D-isoAsn-L-Ala)-:
1-O-(-L-Ala-D-isoGln-L-Ala)-; or
1-O-(-L-Ala-D-isoAsn-L-Ala)-.

Improved anti-infectious activity of the other compounds of the invention may manifest itself upon using them at higher doses, particularly inasmuch as they are substantially free of toxicity and pyrogenicity at much higher doses.

(3) Anti-infectious activity of the compounds of the invention with respect to other micro-organisms Similar anti-infectious activity was observed (particularly with the preferred compound) in mice challenged by Pneumococci, Listeria, *P.aeruginosa* and *S.pneumoniae*.

Dis. 1973, 128, 349). It allows the detection of extremely small quantities of endotoxins. For instance 0.01 µg/ml of lipopolysaccharide (LPS-extracted from *Escherichia coli*) induces a positive reaction.

With L-alanyl-D-isoglutaminyl-L-alanyl-glycerol-3-mycolate in a concentration as high as 100 µg/ml, the test was negative, thereby establishing that the product according to the invention is free of endotoxic activity.

The products according to the invention are thus all

TABLE II

| Treatment i.v.at day-1 compound | Dose (µg) | No/ total | Survival at day 10 of infection* Protection** (%) |
|---|---|---|---|
| 1-O—(L—Ala—D—isoGln—L—Ala)—glycerol-3-mycolate | — 100 | 3/40 31/40 | 70 $p < 0.01$ |
| 1-O—(D—isoGln—L—Ala)—glycerol-3-mycolate | — 100 | 5/48 28/49 | 47 $p < 0.01$ |
| 1-O—(L—Ala)—glycerol-3-mycolate | — 100 | 4/40 16/40 | 35 $p < 0.01$ |
| 1-O—(β—Ala—D—isoGln—L—Ala)—gylcerol-3-mycolate | — 100 | 4/32 12/32 | 25 $p < 0.05$ |
| 1-O—(L—Ala—D—isoAsn—L—Ala)—gylcerol-3-mycolate | — 100 | 4/32 16/32 | 37 $p < 0.01$ |
| 1-O—(L—Ala—D—Gln—L—Ala)—glycerol-3-mycolate | — 100 | 4/32 8/32 | 12 NS |
| 1-O—(L—Ala—L—isoGln—L—Ala)—glycerol-3-mycolate | — 100 | 3/32 7/32 | 12 NS |
| DP—L—Ala—decyl ester | — 100 | 3/24 1/24 | 0 |
| DP—L—Ala—pentadecylester | — 100 | 3/32 4/32 | 4 NS |
| 1-O—(DP—L—Ala)—glycerol-3-monostearate | — 100 | 2/24 4/24 | 8 NS |
| 1-O—(DP—L—Ala)—glycerol-2,3-distearate | 2/24 100 | 5/24 | 12 NS |
| 1-O—(DP—L—Ala)—glycerol-3-corynomycolate | — 100 | 3/32 11/32 | 28 $p < 0.05$ |

*Infection by the intramuscular route with $1.5 \times 10^4$ viable organisms.
**Estimated by the difference between percentages of survivors in treated group and its respective control group.

(a) Toxicity study

The innocuousness of L-alanyl-D-isoglutaminyl-L-alanyl-glycerol-3-mycolate has been shown in adrenalectomized mice. It is well known that adrenalectomy makes mice extremely sensitive to the lethal effect of endotoxins ($LD_{50}$ 0.02 µg).

100 µg of product injected intravenously into five adrenalectomized mice did not cause death of any of them.

(b) Study of pyrogenic effect

A pyrogenicity test was run on rabbits according to the European Pharmacopoeia, Vol. 2, 1971, pp. 58–60. As it is well known, rabbits are very sensitive to endotoxin. A febrile response can be induced by $0.7 \, 10^{-9}$ g/kg. The injection of the product caused no hyperthermizing effect at doses as high as 5 mg/kg of body weight.

(c) Limulus assay

This test was carried out according to the method described by ELIN R. J. and WOLFF S. M. (J.Infect.- the more remarkable as their anti-infectious activity is not counterbalanced by undesirable side-effects, such as pyrogenicity.

We claim:

1. A compound of formula

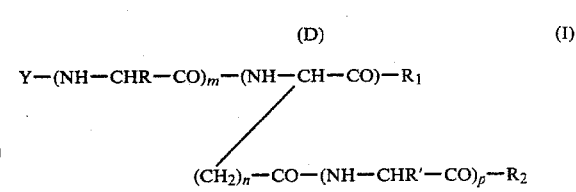

in which
(NH—CHR—CO) is glycyl, beta-alanyl, L-alanyl, L-seryl, L-valyl or L-prolyl and (NH—CHR'—CO) is glycyl, L-alanyl, beta-alanyl, L-arginyl, L-asparagyl, L-cystyl, L-glutaminyl, L-histidyl, L-hydroxyprolyl, L-isoleucyl, L-leucyl, L-methionyl, L-phenylalanyl, L-prolyl, L-seryl, L-threonyl, L-tryptophyl and L-valyl, m is zero or 1, n is 1 or 2, p is 0 or 1, Y is either H or an acyl group with up to 4 carbon atoms, $R_1$ is selected from —OH, alkoxy groups up to —$OC_9H_{19}$, $NH_2$, or an amino group mono or di-substituted by lower alkyl group having up to 9 carbon atoms, $R_2$ is a lipophilic group having the formula —OX, —$OCH_2$—$CH_2O$—COX or —$OCH_2$—CHOH—$CH_2OX$ wherein X is an alkyl linear or branched, saturated or unsaturated group, optionally substituted with hydroxy, carbonyl, carboxyl or aryl groups or a cyclopropane ring, said X containing at least 30 carbon atoms, or the pharmaceutically acceptable salts thereof.

2. The compound of claim 1 wherein the alkoxy group represented by $R_1$ is —$OCH_3$, —$OC_2H_5$ or $OC_3H_7$.

3. The compound of claim 1 wherein X contains from about 80 to about 90 carbon atoms.

4. The compound of claim 1 wherein n is 1.

5. The compound of claim 1 wherein n is 2.

6. The compound of claim 1 wherein m is 1.

7. The compound of claim 6 wherein the aminoacyl residue NH—CHR—CO is L-alanyl.

8. The compound of claim 1 wherein $R_2$ is glycerol-3-mycolate or glycerol-coryno-mycolate.

9. The compound of claim 1, 1-O(L-alanyl-D-isoglutaminyl-L-alanyl)-glycerol-3-mycolate in which the mycolate group contains about 80 to about 90 carbon atoms.

10. The compound of claim 1 of the formula:

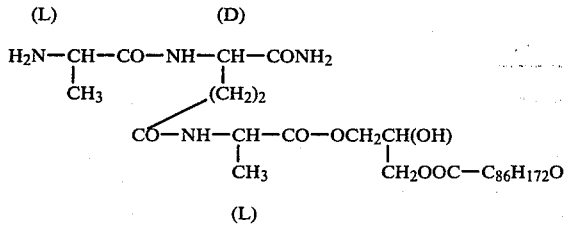

11. The compound of claim 1 selected from the group consisting of:
1-O(L-alanyl-D-isoglutaminyl)-glycerol-3-mycolate,
1-O(L-alanyl-D-isoglutaminyl)-L-alanyl)-glycerol-3-coryno-mycolate, and
1-O(L-alanyl-D-isoglutaminyl)-glycerol-3-coryno-mycolate 12. The compound of claim 1 selected from the group consisting of:
1-O(beta-Ala-D-isoGln-L-Ala)-glycerol-3-mycolate,
1-O(L-Ala-D-isoAsn-L-Ala)-glycerol-3-mycolate, and
1-O(L-Ala-D-Gln-L-Ala)-glycerol-3-mycolate.

13. The compound of claim 5 wherein m is 1 and the NH—CHR—CO residue is glycyl, L-seryl, L-valyl, or L-prolyl.

14. The compound of claim 1 wherein the group of the formula

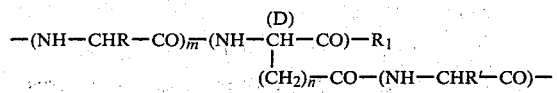

is selected from the group consisting of:
1-O-(L-Ala-D-isoGln)-,
1-O(L-Ala-D-isoAsn)-,
1-O-(-D-isoGln-L-Ala)-,
1-O(-D-isoAsn-L-Ala)-,
1-O-(L-Ala-D-isoGln-L-Ala)-, and
1-O-(-L-Ala-D-isoAsn-L-Ala)-.

15. The salts of claim 1 which are the acid addition salts.

16. A biologically active, non-pyrogenic composition having anti-infectious activity comprising a compound of claim 1 in a biologically active amount with a biologically acceptable carrier.

17. The composition of claim 16 wherein the alkoxy group represented by $R_1$ is —$OCH_3$, —$OC_2H_5$ or $OC_3H_7$.

18. The composition of claim 16 wherein X contains from about 80 to about 90 carbon atoms.

19. The composition of claim 16 wherein n is 1.

20. The composition of claim 16 wherein n is 2.

21. The composition of claim 16 wherein m is 1.

22. The composition of claim 16 wherein the aminoacyl residue NH—CHR—CO is L-alanyl.

23. The composition of claim 16 wherein $R_2$ is glycerol-3-mycolate or glycerol-coryno-mycolate.

24. The composition of claim 16, 1-O(L-alanyl-D-isoglutaminyl-L-alanyl)-glycerol-3-mycolate in which the mycolate group contains about 80 to about 90 carbon atoms.

25. The composition of claim 16 of the formula:

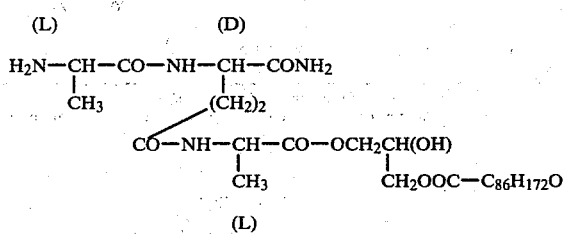

26. The composition of claim 16 selected from the group consisting of:
1-O(L-alanyl-D-isoglutaminyl)-glycerol-3-mycolate,
1-O(L-alanyl-D-isoglutaminyl)-L-alanyl)-glycerol-3-coryno-mycolate, and
1-O(L-alanyl-D-isoglutaminyl)-glycerol-3-coryno-mycolate.

27. The composition of claim 16 selected from the group consisting of:
1-O(beta-Ala-D-isoGln-L-Ala)-glycerol-3-mycolate,
1-O(L-Ala-D-isoAsn-L-Ala)-glycerol-3-mycolate, and
1-O(L-Ala-D-Gln-L-Ala)-glycerol-3-mycolate.

28. The composition of claim 16 wherein m is 1 and the NH—CHR—CO residue is glycyl, L-seryl, L-valyl or L-prolyl.

29. The composition of claim 16 wherein the group of the formula $$-(NH-CHR-CO)_{\overline{m}}-(NH-\overset{(D)}{\underset{|}{CH}}-CO)-R_1$$
$$(CH_2)_{\overline{n}}-CO-(NH-CHR'-CO)-$$

is selected from the group consisting of:
1-O-(L-Ala-D-isoGln)-,
1-O(L-Ala-D-isoAsn)-,
1-O-(-D-isoGln-L-Ala)-,
1-O-(-D-isoAsn-L-Ala)-,
1-O-(L-Ala-D-isoGln-L-Ala)-, and
1-O-(-L-Ala-D-isoAsn-L-Ala)-.

30. A dosage unit comprising a composition of claim 16, 17, 18, 19, 20, 21, 22, 23, 24, 25, 26, 27, 28, or 29 in an amount containing from about 10 to about 10,000 μg of the active compound.

31. The therapeutic method for controlling bacterial infection which comprises administering a biologically active composition comprising a compound of the formula:

$$Y-(NH-CHR-CO)_m-(NH-\overset{(D)}{\underset{|}{CH}}-CO)-R_1 \quad I$$
$$(CH_2)_n-CO-(NH-CHR-CO)_p-R_2$$

in which
(NH—CHR—CO) is glycyl, beta-alanyl, L-alanyl, L-seryl, L-valyl or L-prolyl and (NH—CHR'—CO) is glycyl, L-alanyl, beta-alanyl, L-arginyl, L-asparagyl, L-cystyl, L-glutaminyl, L-histidyl, L-hydroxyprolyl, L-isoleucyl, L-leucyl, L-methionyl, L-phenylalanyl, L-prolyl, L-seryl, L-threonyl, L-tryptophyl and L-valyl,
m is zero or 1,
n is 1 or 2,
p is 0 or 1,
Y is either H or an acyl group with up to 4 carbon atoms,
$R_1$ is selected from —OH, alkoxy groups up to —$OC_9H_{19}$, $NH_2$, or an amino group mono or disubstituted by lower alkyl group having up to 9 carbon atoms,
$R_2$ is a lipophilic group having the formula —OX, —$OCH_2$—$CH_2O$—COX or —$OCH_2CHOH$—$CH_2OX$ wherein X is an alkyl linear or branched, saturated or unsaturated group, optionally substituted with hydroxy, carbonyl, carboxyl or aryl groups or a cyclopropane ring, said X containing at least 30 carbon atoms, or the pharmaceutically acceptable salts thereof in a biologically acceptable carrier, the composition being administered in an effective amount to control the bacterial infection.

32. The method of claim 31 which is carried out virtually without pyrogenic effect.

33. The method of claim 31 wherein the bacterial infection is caused by one of the following:
Pneumococci, Listeria, P.aeruqinosa and S.pneumoniae.

34. The method of claim 31 wherein the compound is selected from one of the following:
1-O(L-alanyl-D-isoglutaminyl)-glycerol-3-mycolate,
1-O(L-alanyl-D-isoglutaminyl)-L-alanyl)-glycerol-3-coryno-mycolate, and
1-O(L-alanyl-D-isoglutaminyl)-glycerol-3-coryno-mycolate
1-O(beta-Ala-D-isoGln-L-Ala)-glycerol-3-mycolate,
1-O(L-Ala-D-isoAsn-L-Ala)-glycerol-3-mycolate, and
1-O(L-Ala-D-Gln-L-Ala)-glycerol-3-mycolate.

35. The method of claim 31 wherein the compound is:

$$\begin{array}{c}
\overset{(L)}{H_2N-CH-CO-NH}-\overset{(D)}{CH-CONH_2} \\
| \quad\quad\quad\quad\quad\quad | \\
CH_3 \quad\quad\quad (CH_2)_2 \\
CO-NH-CH-CO-OCH_2CH(OH) \\
| \quad\quad\quad\quad\quad\quad | \\
CH_3 \quad\quad\quad CH_2OOC-C_{86}H_{172}O \\
(L)
\end{array}$$

36. The method of claim 31 wherein the amount in which the compound is administered is from about 10 to 10,000 micrograms.

* * * * *